United States Patent
Fokkenrood et al.

(10) Patent No.: US 10,772,602 B2
(45) Date of Patent: Sep. 15, 2020

(54) SYSTEM FOR MONITORING A USE OF A MEDICAL DEVICE

(71) Applicant: KONINKLIJKE PHILIPS N.V., Eindhoven (NL)

(72) Inventors: Steven Antonie Willem Fokkenrood, 's-Hertogenbosch (NL); Aloysius Cornelis Johannes Stroucken, Eindhoven (NL); Harm Jan Willem Belt, Weert (NL); Alexander Franciscus Kolen, Eindhoven (NL); Nenad Mihajlovic, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 664 days.

(21) Appl. No.: 15/526,515

(22) PCT Filed: Nov. 24, 2015

(86) PCT No.: PCT/EP2015/077510
§ 371 (c)(1),
(2) Date: May 12, 2017

(87) PCT Pub. No.: WO2016/083379
PCT Pub. Date: Jun. 2, 2016

(65) Prior Publication Data
US 2017/0311925 A1    Nov. 2, 2017

(30) Foreign Application Priority Data
Nov. 25, 2014    (EP) ..................................... 14194648

(51) Int. Cl.
*A61B 8/00*    (2006.01)
*A61B 8/12*    (2006.01)
(Continued)

(52) U.S. Cl.
CPC .............. *A61B 8/4438* (2013.01); *A61B 8/12* (2013.01); *A61B 8/4477* (2013.01);
(Continued)

(58) Field of Classification Search
CPC ................................ A61B 8/4438; A61B 8/00
See application file for complete search history.

(56) References Cited

U.S. PATENT DOCUMENTS 5,552,645 A    9/1996  Weng
5,651,780 A    7/1997  Jackson et al.
(Continued)

FOREIGN PATENT DOCUMENTS

JP    H06205776 A    7/1994
JP    H08229042 A    9/1996
(Continued)

OTHER PUBLICATIONS

Mung, J. et al., "A non-disruptive technology for robust 3D tool tracking for ultrasound-guided interventions", Medical Image computing and computer-assisted intervention—MICCAI 2015, 18th International conference, Munich, Germany, pp. 153-160.
(Continued)

*Primary Examiner* — James M Kish

(57) ABSTRACT

The invention provides a system (1) for determining an identification characteristic of a medical device (3) carrying at least an ultrasound emitter/sensor element (321). The identification characteristic is based on a detection signal from the ultrasound emitter/sensor element (321) upon a drive signal. The system (1) can identify the medical device from a database (211,511) of known medical devices. Furthermore, the system (1) can update the duration and frequency of use of the medical device (3) and it can prohibit further use of the medical device (3) when a predetermined limit of use is exceeded.

15 Claims, 15 Drawing Sheets

(51) Int. Cl.
    *A61B 8/08*     (2006.01)
    *G01S 15/89*     (2006.01)
    *B06B 1/02*     (2006.01)
    *G01S 7/52*     (2006.01)
    *B06B 1/06*     (2006.01)

(52) U.S. Cl.
    CPC .............. *A61B 8/4483* (2013.01); *A61B 8/52* (2013.01); *A61B 8/565* (2013.01); *B06B 1/0207* (2013.01); *G01S 7/5205* (2013.01); *G01S 15/8909* (2013.01); *B06B 1/0292* (2013.01); *B06B 1/06* (2013.01); *B06B 2201/40* (2013.01); *B06B 2201/76* (2013.01)

(56) References Cited

U.S. PATENT DOCUMENTS

| | | | |
|---|---|---|---|
| 5,991,355 A | 11/1999 | Dahlke | |
| 6,659,955 B1* | 12/2003 | Marian, Jr. | A61B 8/00 600/437 |
| 7,118,564 B2 | 10/2006 | Ritchie et al. | |
| 7,730,865 B2 | 6/2010 | Yokoi | |
| 7,987,001 B2 | 7/2011 | Teichman et al. | |
| 8,696,572 B2 | 4/2014 | Canfield | |
| 9,256,947 B2 | 2/2016 | Gauthier et al. | |
| 2003/0036704 A1* | 2/2003 | Cerofolini | G01S 7/5208 600/437 |
| 2003/0135115 A1 | 7/2003 | Burdette et al. | |
| 2005/0259517 A1* | 11/2005 | Sifferman | G01S 7/524 367/87 |
| 2005/0288584 A1 | 12/2005 | McMorrow et al. | |
| 2006/0025756 A1* | 2/2006 | Francischelli | A61N 7/02 606/27 |
| 2006/0039996 A1 | 2/2006 | Palmer | |
| 2007/0239006 A1 | 10/2007 | Kamiyama et al. | |
| 2007/0293762 A1 | 12/2007 | Sawada et al. | |
| 2010/0305450 A1* | 12/2010 | Kosaku | A61B 8/14 600/459 |
| 2011/0040185 A1* | 2/2011 | Matsumura | A61B 8/00 600/443 |
| 2011/0040186 A1* | 2/2011 | Matsumura | A61B 5/6843 600/443 |
| 2011/0105904 A1 | 5/2011 | Watanabe | |
| 2012/0203095 A1 | 8/2012 | Krieger et al. | |
| 2013/0116538 A1* | 5/2013 | Herzog | A61B 8/4254 600/407 |
| 2013/0299577 A1 | 11/2013 | Bek et al. | |
| 2014/0187919 A1 | 7/2014 | Parthasarathy et al. | |
| 2015/0032004 A1* | 1/2015 | Kim | A61B 8/4444 600/443 |
| 2016/0074008 A1* | 3/2016 | Eda | G01S 15/895 600/447 |

FOREIGN PATENT DOCUMENTS

| | | |
|---|---|---|
| JP | 2006346477 A | 12/2006 |
| WO | 2006006107 A1 | 1/2006 |
| WO | 2013158154 | 10/2013 |

OTHER PUBLICATIONS

Hakime, A. et al., "Electromagnetic—tracked biopsy under ultrasound guidance: preliminary results", CardioVascular and Interventional Radiology, Sep. 27, 2011, vol. 35, nr: 4, pp. 898-905.

* cited by examiner

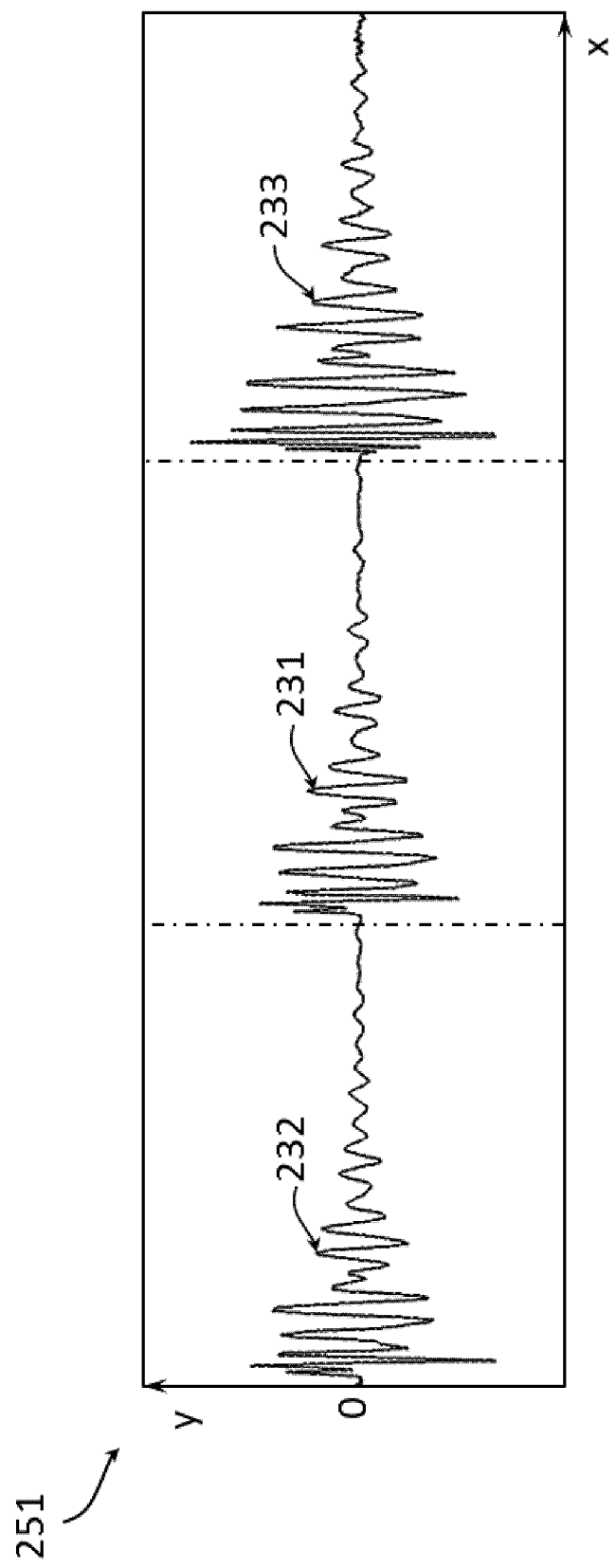

SYSTEM FOR MONITORING A USE OF A MEDICAL DEVICE

CROSS-REFERENCE TO PRIOR APPLICATIONS

This application is the U.S. National Phase application under 35 U.S.C. § 371 of International Application Serial No. PCT/EP2015/077510, filed on Nov. 24, 2015, which claims the benefit of European Patent Application No. 14194648.3, filed on Nov. 25, 2014. These applications are hereby incorporated by reference herein.

FIELD OF THE INVENTION

The invention relates to a system for identifying a medical device. The invention further relates to a system for monitoring and controlling use of medical devices.

BACKGROUND OF THE INVENTION

Use of medical devices for diagnosing or treating conditions of the body can result in entrapping biological material on the surface or within the structure of the medical device. Cleaning and subsequent sterilization of medical devices after use may provide sufficiently safe conditions for reuse. However, material fatigue and chemical reactions during sterilization may result in unsafe conditions for use of medical devices after repetitive sterilization cycles.

U.S. Pat. No. 5,651,780 presents a catheter that electronically retains an identification code that uniquely identifies the predetermined operating characteristics. The catheter is capable of transmitting the identification code to an external reader in response to a predetermined prompt. An associated apparatus reads the identification code and compares it to predetermined operating criteria. The identification code can be pre-programmed on a solid state micro-chip integrated into the catheter handle. Alternatively the identification means can be based on a resistor with a prescribed electrical resistance value, integrated into the catheter, and the electrical resistance value becomes the identification code when sensed by the associated apparatus. The apparatus will not permit interaction with the functional catheter component if the identification code indicates that the functional characteristics of the catheter are not suited for the intended interaction. The catheter can store usage information on the solid state micro-chip, to prevent reuse.

Integration of specific electronic devices such as microchips for retaining an identification code or resistors for identifying the medical device based on a specific resistance value requires also connection to the electronics for read out and control purposes. Incorporating additional electronics in tightly packed medical devices like catheters or interventional needles presents a serious technical challenge due to severe dimensional requirements of such medical devices. Furthermore, functional requirements regarding connection of the medical devices to operating systems such as flexibility and handling freedom is conflicting with addition of specific connections required for the identification microchip or electrical resistance to the read out electronics. Any additional electronic component integrated into the medical device, as well as long transmission lines between read-out electronics and medical device represent potential electromagnetic interference burden on detection signals measured during the intended use of the medical device comprising ultrasound emitter/sensor elements.

WO2008032239A2 presents a medical system for generating comprehensive simulated report of the system's capabilities for demonstration and validation purposes, the medical system comprising an ultrasound imaging probe, an ultrasound signal path, a processing unit, disk drive and a report printer. The comprehensive report simulation is realised with the following steps: storing patient data and raw data corresponding to signals in a first database contained in the medical system; processing the raw data to obtain data corresponding to visually conceivable information; using the patient data and the visually conceivable information to create a report simulation.

SUMMARY OF THE INVENTION

It is an object of the invention to provide a system for identifying medical devices comprising ultrasound emitter/sensor element, without integration of additional passive and/or active electronics specific for identification purposes.

According to the invention, this object is realized by a system for recognizing an identification characteristic of a medical device carrying at least one ultrasound emitter/sensor element, the system comprising an apparatus arranged to be operatively coupled to the medical device, wherein the apparatus is arranged to send a drive signal to the ultrasound emitter/sensor element and to receive a detection signal from the ultrasound emitter/sensor element, the apparatus further comprising a processor, wherein the processor is operable to process detection signals form the ultrasound emitter/sensor to determine an identification characteristic of the medical device, and wherein the processor is further operable to recognize the identification characteristic of the medical device from a database of known identification characteristics of medical devices subsequent to a coupling of the medical device to the apparatus.

The advantage of the invention resides in using existing components of the system for determining the identity of medical devices comprising at least one ultrasound emitter/sensor element, without further need for integration of specific electronic devices for retaining an identification code and electronics for read out and controlling purposes.

An ultrasound emitter/sensor element comprises an active part, which generates ultrasound waves upon an electrical drive signal, and passive parts for coupling acoustic waves only into the desired medium. The passive parts comprise backing material for attenuating transmission of ultrasound waves in undesired directions (e.g. proximal shaft of the device), and matching layers for efficiently coupling ultrasound waves into a medium in the desired direction (e.g. anatomical structures, air, etc.).

An ultrasound emitter/sensor element integrated into the medical device comprises at least an acoustic coupling material fixed on the face of the active part of the ultrasound emitter/sensor element. Upon an electrical drive pulse sequence at certain intensity sent by the apparatus, the active part generates ultrasound waves, which scatter and reflect within the acoustical coupling material. The active part of the ultrasound emitter/sensor element detects the ultrasound waves that reach its surface and transmits the detection signal to the processor of the apparatus, which processes an identification characteristic of the ultrasound emitter/sensor element, hence an identification characteristic of the medical device. Such an identification characteristic may be a feature vector comprising a subset of data samples of the detected radiofrequency signal by the ultrasound emitter/sensor element. The practical subset of data samples is limited within the thickness of the acoustical coupling materials in the direction of transmission of ultrasound waves, which depends only on the ultrasound emitter/sensor construction and is independent on the circumstances of the surrounding. Ultrasound signals detected from and beyond the interface of the acoustical coupling material with the surrounding are strongly dependent on the circumstances of the surrounding and therefore they are not suitable for identification purposes of the ultrasound emitter/sensor element.

Ultrasound emitter/sensor elements present unique response to electrical drive pulse sequence due to small inherent manufacturing imperfections and/or deviations in the acoustical stack comprising the active emitter/sensor element, backing materials, acoustic coupling layers, and bonding materials. Furthermore, tiny imperfections may voluntarily be added in the manufacturing process of the ultrasound emitter/sensor elements for the purpose of creating more differentiating response of the ultrasound emitter/sensor elements to the same electrical drive pulse sequence.

The ultrasound emitter/sensor elements may originate from a piezoelectric ultrasound emitter/sensor array or from a capacitive micro-machined ultrasound emitter/sensor array. Ultrasound emitter/sensor arrays provide an increased aperture for receiving ultrasound scattering and reflection from anatomical structures upon impinging ultrasound waves.

Multiple ultrasound emitter/sensor elements of the array enable combination of the individual identification characteristics. In an embodiment of the invention the combination of individual characteristics is achieved by constructing a feature vector of the medical device by assembling the individual feature vectors of ultrasound emitter/sensor elements.

Ultrasound emitter/sensor elements in a medical device may be oriented in different directions. In case of anatomical structures of interest positioned at various orientations with respect to the medical device (e.g. heart anatomy with respect to a catheter located in a heart chamber) it is advantageous that ultrasound emitter/sensor elements are oriented in various directions for providing information on tissue property together with the relevant position of the tissue region in the heart anatomy.

In an embodiment of the system, the processor is operable to update a database of known identification characteristics of medical devices by adding to the database the identification characteristic of the medical device coupled to the apparatus. The database may be stored in an internal memory unit of the apparatus or alternatively it may be stored in a memory unit of an external server. The apparatus may be arranged to communicate through wired or wireless communication continuously or at regular intervals with the external server for transmitting and/or receiving at least an identification characteristic of a medical device.

In an embodiment of the system, the processor is operable to recognize the identification characteristic of the medical device from a database of known identification characteristics of medical devices based on a quadratic norm of feature vector differences.

In a further embodiment of the system, the processor is operable to update information in the database about a duration and a frequency of use of the medical device. Therefore, the extent of use of medical devices comprising integrated ultrasound emitter/sensor elements can be logged.

In a further embodiment of the invention the processor is operable to send a warning signal to the user of the system when a predetermined use of a medical device is exceeded. The warning signal may be a visual signal or a text displayed on a screen of the system, a tactile feedback, an audible signal, etc.

In another embodiment of the invention the apparatus is operable to update the database of known identification characteristics of medical devices on the external server with a warning message for use of the medical device exceeding the predetermined limit. The main benefit is the possibility for logging use of medical devices deviating from the recommended limitation, indifferent from how the user of the system reacts upon prompted warning signals.

In an alternative embodiment of the system, the apparatus is arranged to discontinue the use of at least one ultrasound emitter/sensor element when a predetermined use of the medical device is exceeded. The main benefit is to discourage reuse of medical devices in potentially unsafe conditions where multiple reuse of the medical device requires repetitive sterilization cycles, which may result in unsafe conditions due to material fatigue or undesired chemical reactions.

In yet another embodiment, the system further comprises an energy source unit for energy application to a tissue, wherein the apparatus is arranged to disallow transmission of energy from the energy source unit to the medical device when a predetermined use of the medical device is exceeded. A medical device operable to apply energy to a tissue may potentially be a single use disposable device. Unsafe use of the medical device is discouraged by recognizing the medical device attempted to be used in an inappropriate manner, followed by subsequently disabling transmission of energy to the medical device.

Additional aspects and advantages of the invention will become more apparent from the following detailed description, which may be best understood with reference to and in conjunction with the accompanying drawings.

BRIEF DESCRIPTION OF THE DRAWINGS

In the drawings:

FIG. 7 shows a graphical illustration of a response function used for determining an identification characteristic of a medical device comprising multiple ultrasound emitter/sensor elements.

DETAILED DESCRIPTION OF EMBODIMENTS

Figure 1:
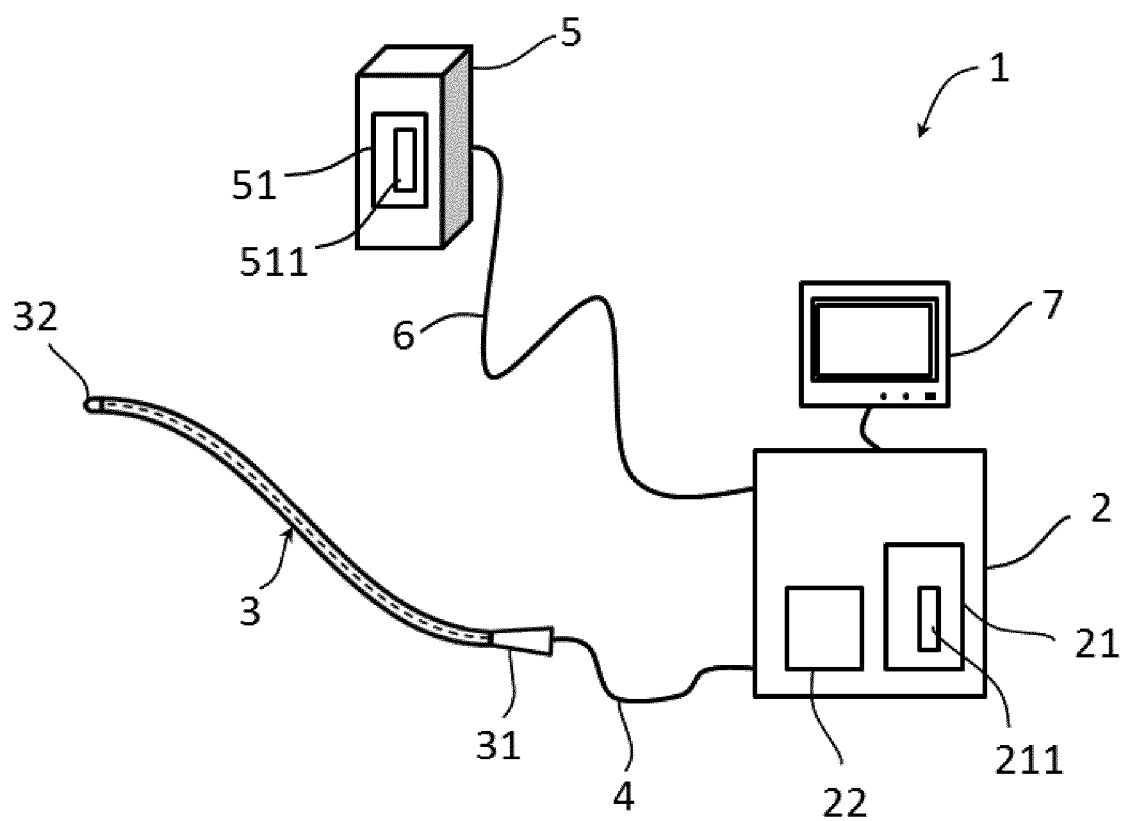
FIG. 1 shows schematically and exemplarily an embodiment of a system according to the invention.

An embodiment of a system 1 according to the invention, shown in FIG. 1, comprises an apparatus 2 operatively coupled to a medical device 3, and a display unit 7 for displaying ultrasound measurement information collected with the medical device 3. The apparatus 2 is arranged to send a drive signal to at least an ultrasound emitter/sensor element integrated into the medical device 3 through a transmission path 4 and to receive a detection signal from the ultrasound emitter/sensor element through the same transmission path. The apparatus 2 further comprises a processor 22, which is operable to process detection signals from the ultrasound emitter/sensor element integrated into a medical device 3.

The apparatus comprises an internal memory unit 21 for storing locally data resulting from processing of detection signals. Alternatively, the internal memory unit may be a removable memory unit. In an embodiment according to the invention the apparatus 2 can be arranged to communicate with an external server 5 through a transmission path 6 for transmitting and/or receiving data resulting from processing of detection signals. The transmission path 6 enables synchronization of data stored in the internal memory unit 21 of the apparatus 2 and data stored in the memory unit 51 of the external server 5.

The transmission path 4 between the medical device and the apparatus 2 as well as the transmission path 6 between the apparatus 2 and the external server 5 may be wired or wireless connection. The display unit 7 may be integrated into the apparatus 2, which may provide advantages for portable systems.

The elongated body of the medical device 3 comprises a proximal end 31 for coupling the medical device to the apparatus 2 through transmission path 4, and a distal end 32. The proximal end 31 of the medical device 3 may directly be coupled to the apparatus 2 without the transmission path 4.

Figure 2:
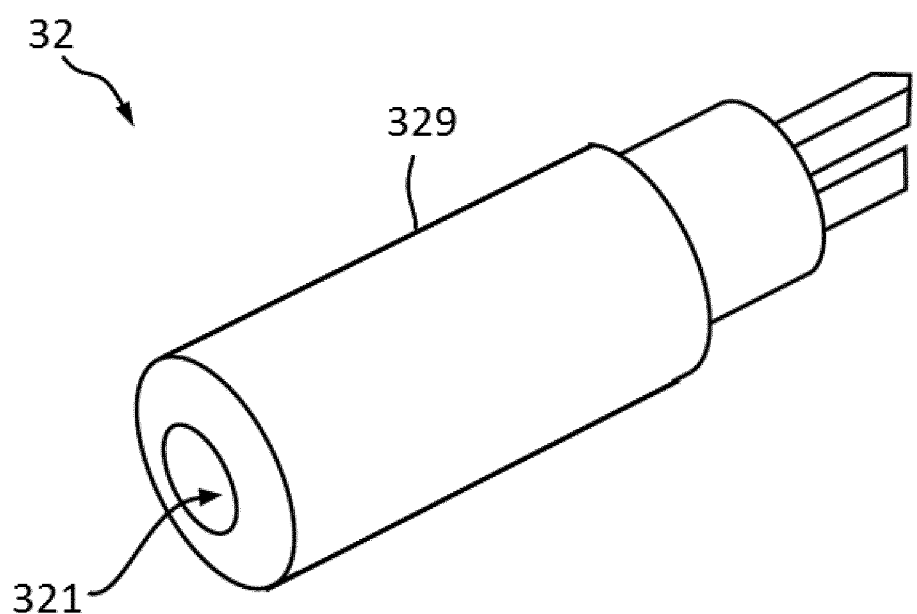
FIG. 2 shows schematically and exemplarily an embodiment of a distal end of a medical device according to the invention.

An embodiment of the distal end 32 of the medical device is schematically and exemplarily presented in FIG. 2. An axially oriented ultrasound emitter/sensor element 321 is integrated into a casing 329. The ultrasound emitter/sensor element 321 can provide information of an anatomy in front of the distal end 32 of the medical device. The material of the casing 329 may have electrical insulating or electrical conductive properties. Electrical insulating materials such as polyether block amides (e.g. PEBAX) present thermoplasticity, therefore the casing can easily be formed. On the other hand, electrical conductive materials (e.g. Platinum-Iridium alloys) are suitable for applying energy to tissue in the form of radiofrequency current.

Figure 3A:
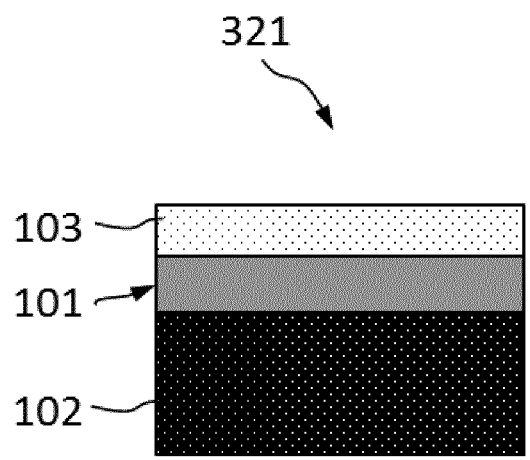
FIGS. 3A and 3B show cross sections of ultrasound emitter/sensor elements for use in a system according to the invention.
Figure 3B:
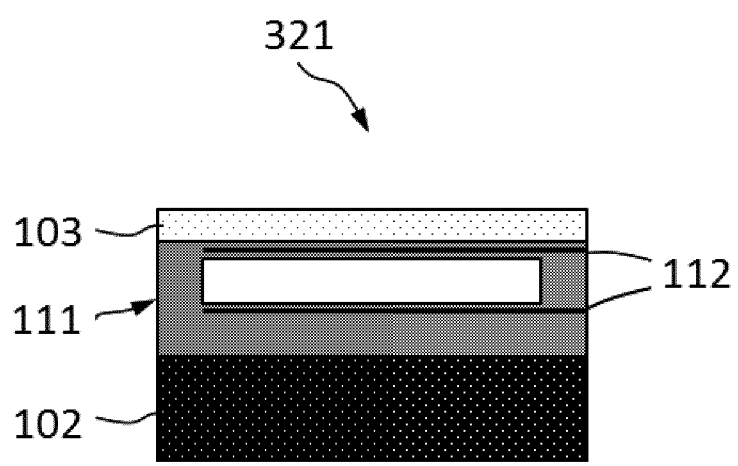
Figure 4:
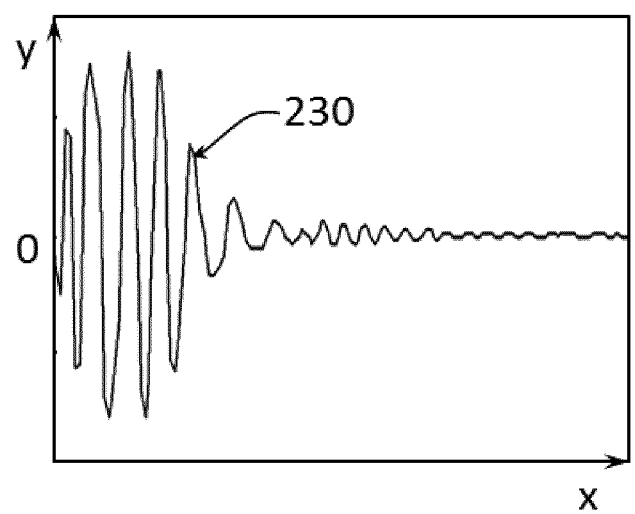
FIG. 4 shows a graphical representation of a detection signal of an ultrasound emitter/sensor element.

The ultrasound emitter/sensor element 321 is a multilayer stack construction, comprising an active part for generating ultrasound waves upon a received electrical drive signal, and passive parts for efficiently coupling acoustic waves into a medium in the desired direction. FIG. 3A shows a cross section of an ultrasound emitter/sensor element 321 comprising a piezoelectric material (e.g. PZT5H, polyvinylidene fluoride) as active part 101. Electrically conductive layers are processed on both faces of the active part 101 for allowing excitation of the piezoelectric material with an electrical drive signal. Alternatively, the active part of an ultrasound emitter/sensor element may be a capacitive micro-machined ultrasound transducer (CMUT) cell 111. A cross section of such an ultrasound emitter/sensor element is schematically illustrated in FIG. 3B. The electrical drive signal is applied on two electrically conductive electrodes 112, one integrated into a membrane and the other one integrated into the membrane supporting substrate. For both cases, when the active element is piezoelectric material 101 or CMUT cell 111, the longitudinal ultrasound waves generated upon a received electrical drive signal transmit in both directions, perpendicular to the faces of the active part. A backing layer 102 may be applied on one side of the active part of the emitter/sensor element in order to rapidly attenuate the ultrasound waves. The backing layer is usually a composite material of scattering particles within a matrix of material efficiently attenuating acoustic waves. On the other face of the active part of the ultrasound emitter/sensor element at least one acoustic coupling layer 103 is processed, which serves multiple purposes such as efficiently coupling ultrasound waves to the surrounding, mechanical, chemical and electrical protection of the active part. Suitable acoustic coupling materials are polydimethylsiloxane (PDMS), various types of polyether block amides (PEBAX), polybutadiene, parylene, etc. Acoustic coupling materials may have various forms with lens effect for focusing or defocusing ultrasound waves towards surrounding. A graphical representation of a detection signal 230 of an ultrasound emitter/sensor element upon a single cycle sinus shape drive signal is shown in FIG. 4. Although for elucidation of the invention a single cycle sinus shape drive signal is used, any other form of drive signal can be applied to the ultrasound emitter/sensor element, provided that the active part of the ultrasound sensor/emitter element is able to generate ultrasound waves upon receiving the respective drive signal.

The detection signal 230 is a radiofrequency (RF) signal received by the apparatus. In the graphical representation they axis represents the amplitude of the RF signal and the x axis represents the depth in the direction of transmission of ultrasound waves. The depth may alternatively be expressed in time of flight of the ultrasound waves, which is the time that it takes for ultrasound waves to travel a distance through a medium surrounding the ultrasound emitter/sensor element.

Reproducibility of conditions of the surrounding wherein the ultrasound waves are transmitted is very low, therefore the scattered and reflected ultrasound waves from the surrounding towards the ultrasound emitter/sensor element are practically variable in time. Influence of the surrounding on the detection signal should preferably be removed in order to use the detection signal for identification purpose of ultrasound emitter/sensor elements.

Identification characteristics of ultrasound emitter/sensor elements should be based on detection signal originating within the multilayer stack shown in FIGS. 3A and 3B. The practical length of the detection signal usable for determining an identification characteristic of the ultrasound emitter/sensor element is determined at the one side by the moment of reaction of the active part of the ultrasound emitter/sensor element to the electrical drive signal, and on the other side by the reflection of ultrasound waves from the interface between the acoustic coupling material and the surrounding. The thickness and composition of the acoustic coupling material 103 is therefore evident. When the thicknesses and compositions of materials in the multilayer stack ultrasound emitter/sensor element are known, then the length of the detection signal usable for identification purposes can be determined based on the speed of sound in the multilayer stack. However, in most practical cases tiny unavoidable variations of thickness, composition and surface finish of the layers make every single ultrasound emitter/sensor element unique, having slightly different length of detection signal usable for identification purposes.

In order to make the invention practically usable for any circumstances of the surrounding, as well as to make it indifferent for ultrasound emitter/sensor elements with known and unknown composition of multilayer stacks, a detection signal is preferably obtained by processing a number of RF detection signal lines of the same ultrasound emitter/sensor element upon identical drive signal over a limited time interval.

The smallest changes in the circumstances of the surrounding can contribute to unstable detection signals, which may manifest in noise and variable signal in time (e.g. relative motion between a medical device and heart tissue). In the preferred embodiment a response function of an ultrasound emitter/sensor element is obtained by removing contributions related to the circumstances of the surrounding from the detection signal with a recursive low-pass filter. The recursive filter may be implemented using the following recurrence relation $$y_d[n] = \alpha \cdot y_d[n-1] + \beta \cdot \{x_d[n] + x_d[n-1]\} \quad \text{(Eq. 1)}$$

where $x_d[n]$ is the RF line sample value at discrete time index n at depth d, whereas $y_d[n]$ is the low-pass filtered RF line sample for the same time and depth indices. The parameters $\alpha$ and $\beta$ are given by $$\alpha = \frac{\tau \cdot f_{PRF} - 1}{\tau \cdot f_{PRF}} \quad \text{(Eq. 2)}$$

$$\beta = \frac{1}{2 \cdot \tau \cdot f_{PRF}} \quad \text{(Eq. 3)}$$

where $f_{PRF}$ is the pulse repletion rate in Hertz and T is a time constant defining the averaging duration in seconds or the effective memory of the recursion.

Figure 5A:
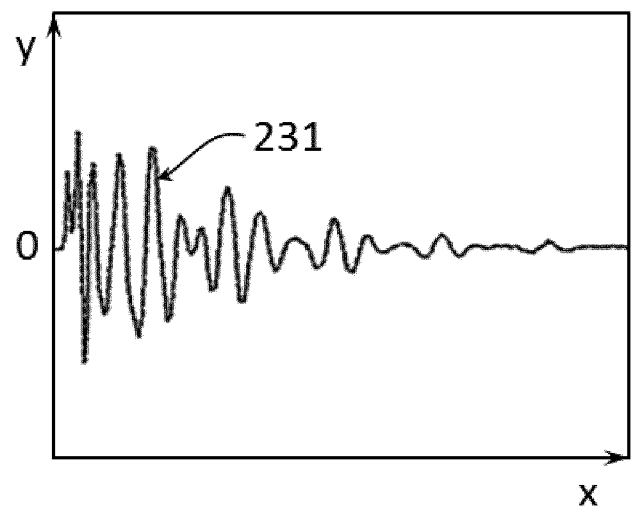
FIGS. 5A and 5B show graphical illustrations of response functions used for determining identification characteristics of medical devices according to the invention.
Figure 5B:
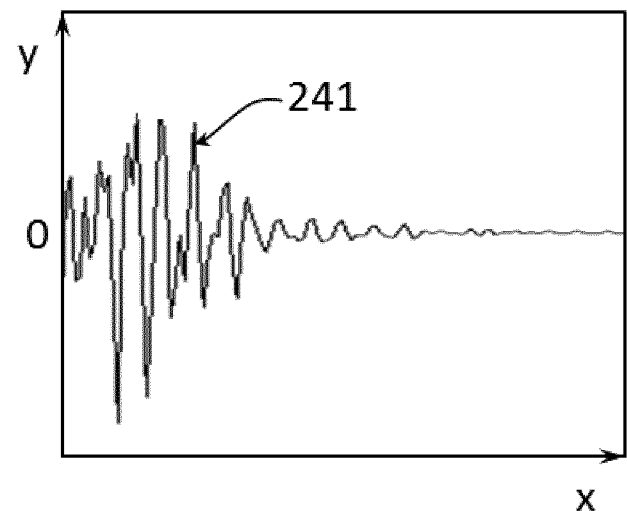

A graphical illustration of a response function 231 of an ultrasound emitter/sensor element 321 comprising piezoelectric material as active part is shown in FIG. 5A. With similar methodology a response function 241 can be obtained for an ultrasound emitter/sensor element comprising CMUT cell 111 as active part, which is exemplarily shown in FIG. 5B.

The processor is arranged to compute a feature vector representing the identification characteristic of the ultrasound emitter/sensor element with $$\vec{f} = [y_{d_0}, y_{d_1}, \ldots, y_{d_{max}}]^T \quad \text{(Eq. 4)}$$

where the elements of the vector are the time-averaged RF line values at various depths to a maximum depth $d_{max}$ considered for computation of the feature vector.

Figure 6A:
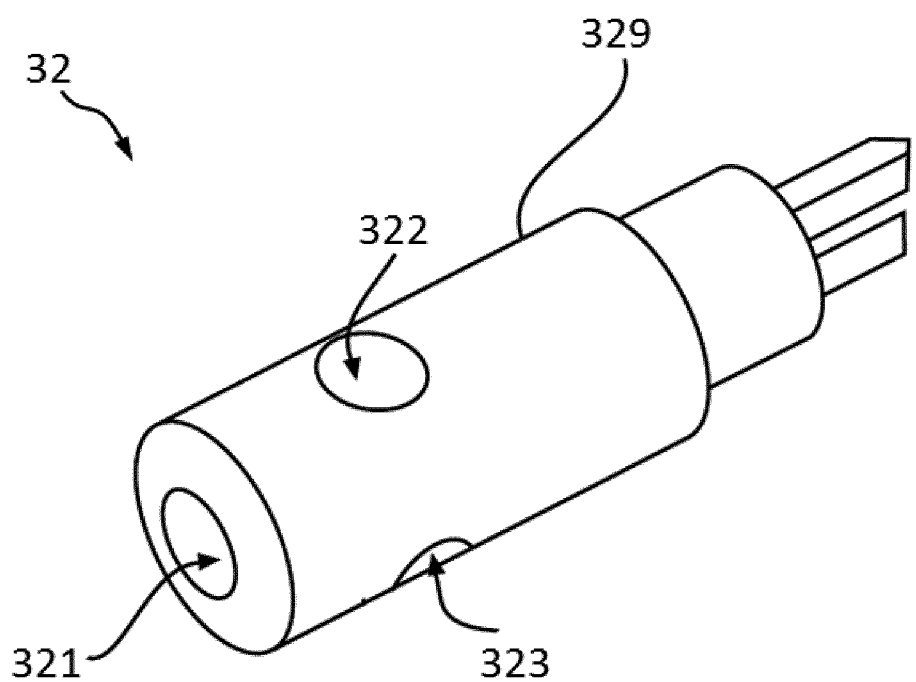
FIG. 6A-6C show schematically and exemplarily embodiments of distal ends of medical devices for use in a system according to the invention.

Multiple ultrasound emitter/sensor elements may be integrated into medical devices. Such embodiments are schematically and exemplarily presented in FIG. 6A-6C. In FIG. 6A, the distal end 32 of a medical device 3 comprises a combination of axially oriented 321 and radially oriented 322,323 ultrasound sensor/emitter elements integrated into a casing 329. This embodiment can provide richer information of an anatomy surrounding the distal end 32 of the medical device.

Multiple ultrasound emitter/sensor elements integrated into a medical device allow combination of the individual identification characteristics. In an embodiment of the invention the combination of individual characteristics is achieved by constructing a feature vector F of the medical device, which may be obtained by assembling the individual feature vectors of ultrasound emitter/sensor elements $$\vec{F} = [f_1^T, f_2^T, \ldots, f_m^T]^T \quad \text{(Eq. 5)}$$

where $f_{1 \ldots m}$ are feature vectors of the individual ultrasound emitter/sensor elements with m number of ultrasound emitter/sensor elements considered for determining the identification characteristic of the medical device.

FIG. 7 shows a response function used for determining the identification characteristic of the medical device 3 illustrated in FIG. 6A, with three ultrasound emitter/sensor elements integrated into the distal end 32. The axial ultrasound emitter/sensor element is considered identical with that of the medical device illustrated in FIG. 2, with a response function 231 represented in FIG. 5A. The response function 251 of the medical device comprises besides the response function 231 of the axial ultrasound emitter/sensor element 321 also the response functions 232 and 233 corresponding to the two radially oriented ultrasound emitter/sensor elements 322 and 323.

Figure 6B:
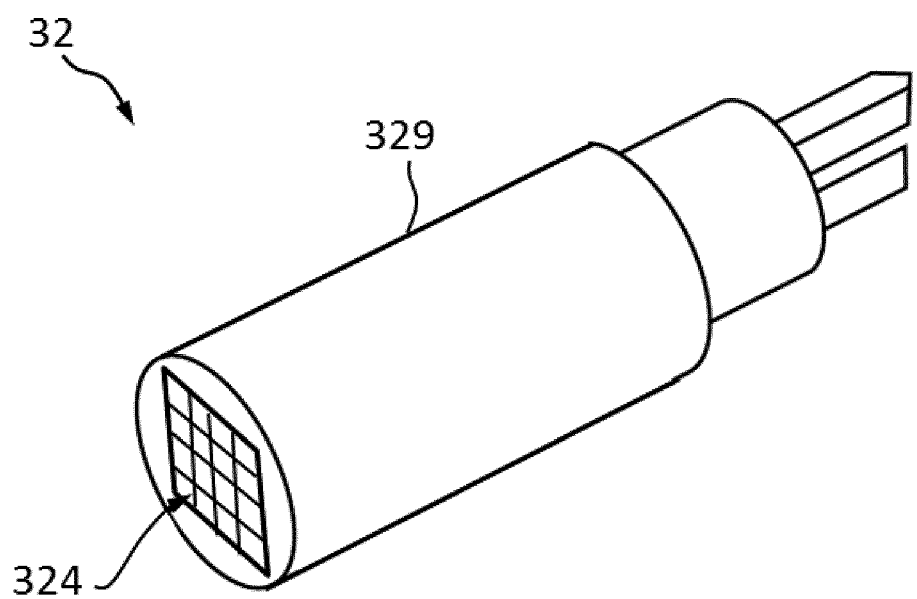
Figure 6C:
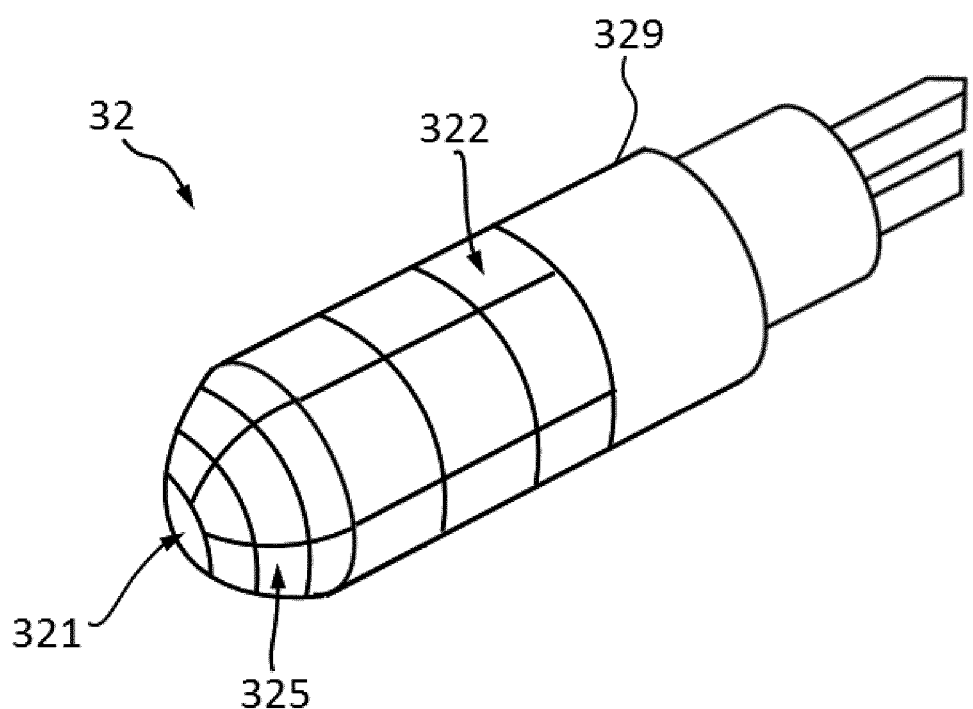

In an alternative embodiment the axially oriented ultrasound emitter/sensor element 321 may originate from a matrix of ultrasound emitter/sensor elements 324, as illustrated in FIG. 6B. This configuration can provide three-dimensional ultrasound information for representation of the anatomy in front of the distal end 32 of the medical device 3. However, for an optimal representation in a three-dimensional rendering of the anatomy surrounding the distal tip, the distal end of the medical device may need a matrix of ultrasound emitter/sensor elements with sufficient coverage. Such an embodiment is schematically and exemplarily shown in FIG. 6C, where the distal end of the medical device comprises axially, obliquely and radially oriented elements, 321, 325 and 322 respectively.

An identification characteristic of a medical device comprising arrays or matrices of ultrasound emitter/sensor elements can be created by assembling multiple individual feature vectors of ultrasound emitter/sensor elements according to Eq. 5.

Once the identification characteristic of the medical device 3 is determined with Eq. 4 and eventually with Eq. 5 according to the configuration of the medical device, the processor 22 of the apparatus 2 is operable to create a database 211 of identification characteristics of medical devices. Furthermore, the processor is operable to update already existing database 211 of known identification characteristics of medical devices by adding to the database the identification characteristic of the medical device 3 coupled to the apparatus 2. The database 211 may be stored in an internal memory unit 21 of the apparatus 2 or alternatively it may be stored in the memory unit 51 of an external server 5.

The database 511 of identification characteristics of known medical devices may be a central database, assembled and/or updated in the production facility of the newly manufactured medical devices.

The apparatus 2 is arranged to communicate continuously or at regular time intervals with the external server 5 for transmitting and/or receiving at least an identification characteristic of a medical device. This enables updating an existing database 511 with identification characteristic of a new medical device subsequent to a coupling of the medical device 3 to the apparatus 2 at the location of first use. The main advantage of such an arrangement is that a central database can be fed with identification characteristics of medical devices manufactured at multiple sites.

Diagnosing and/or treating conditions of a patient may result in entrapping biological material on the surface or within the structure of the medical device. Cleaning and subsequent sterilization of medical devices after use may provide sufficiently safe conditions for reuse of the medical device. However, material fatigue and chemical reactions during sterilization may result in unsafe conditions for subsequent use of the medical device. Therefore, the importance for monitoring the use of medical devices becomes significant in order to avoid adverse effects related to loosing structural components (e.g. catheter components in blood stream) or causing and spreading infectious diseases by reusing medical devices.

Medical devices provided with identification characteristic based on the feature vector of ultrasound emitter/sensor elements can be identified during their use.

The processor 22, operable to process detection signals from the ultrasound emitter/sensor elements, can determine the identification characteristic of the same medical device repeatedly, when it is coupled to the apparatus 2. Furthermore, the processor of the apparatus is operable to recognize the identification characteristic of the medical device from either of the databases 211 or 511 of known identification characteristics of medical devices subsequent to a coupling of the medical device to the apparatus. The drive signal of the ultrasound emitter/sensor element in the moment of identification of the medical device with a known device from the database must be identical in shape and amplitude with the drive signal of the ultrasound emitter/sensor element at the time when the identification characteristic of the medical device was determined for the first time and it was added to the database.

Figure 8A:
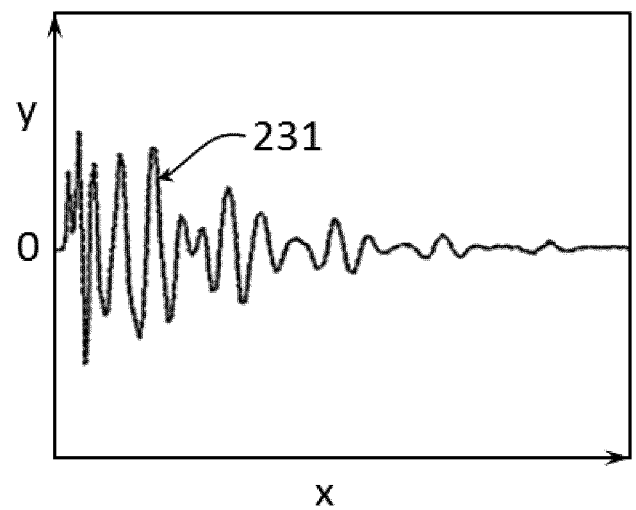
FIG. 8A shows a graphical representation of response functions of a medical device at two different instances.
Figure 8B:
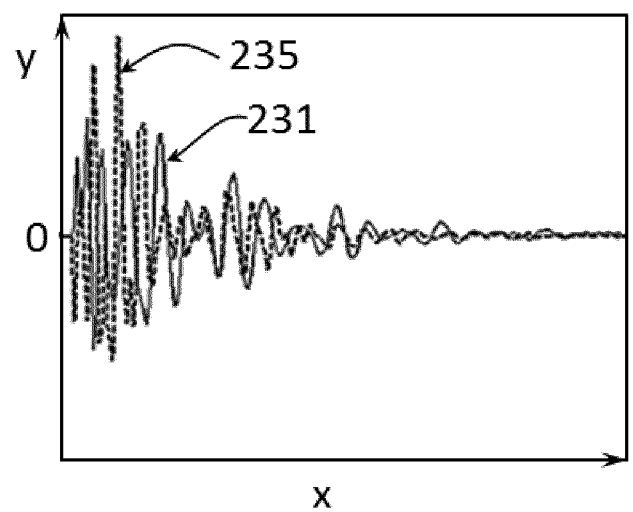
FIG. 8B shows a graphical representation of response functions of two medical devices at two different instances.

A graphical illustration in FIG. 8A shows that response functions of an ultrasound emitter/sensor element determined at two different time instances $t_1$ and $t_2$ are very similar, hence the representations of the response functions 231 completely overlap. Therefore, the identification characteristics of the same ultrasound emitter/sensor element determined at two different time instances based on the feature vectors will also be very similar. On the contrary, in FIG. 8B the response functions 231 and 235 of two dissimilar ultrasound emitter/sensor elements significantly differ, which results in dissimilar identification characteristics.

Figure 9A:
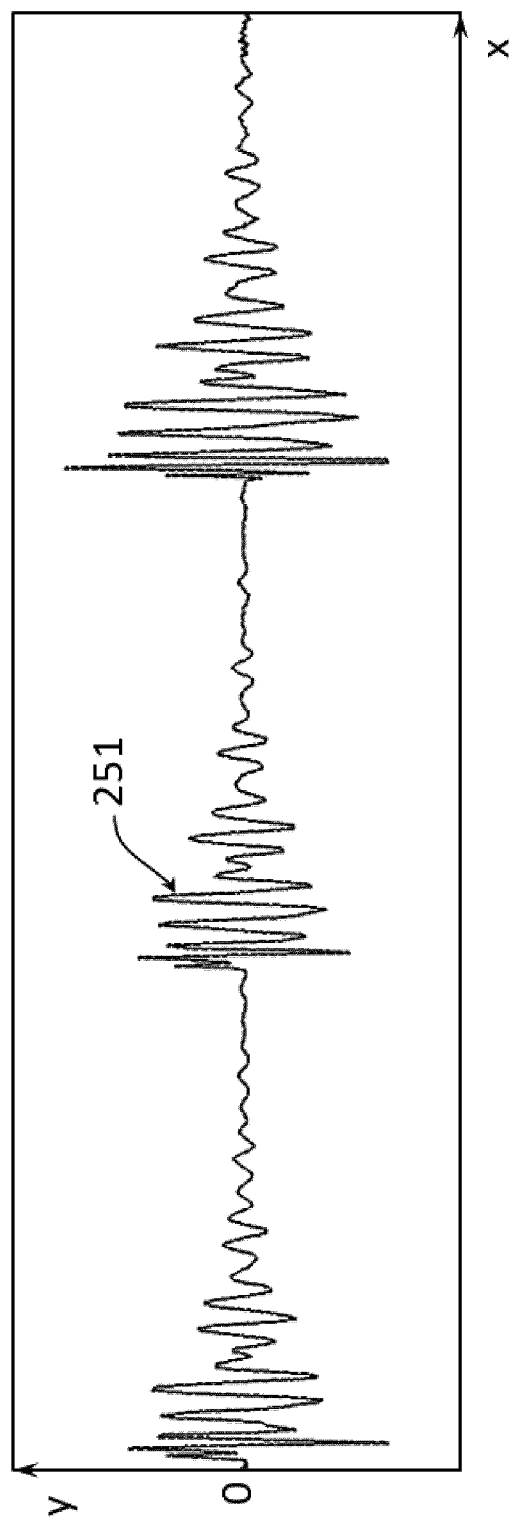
FIG. 9A shows a graphical representation of response functions determined at two different instances for a medical device comprising multiple ultrasound emitter/sensor elements.
Figure 9B:
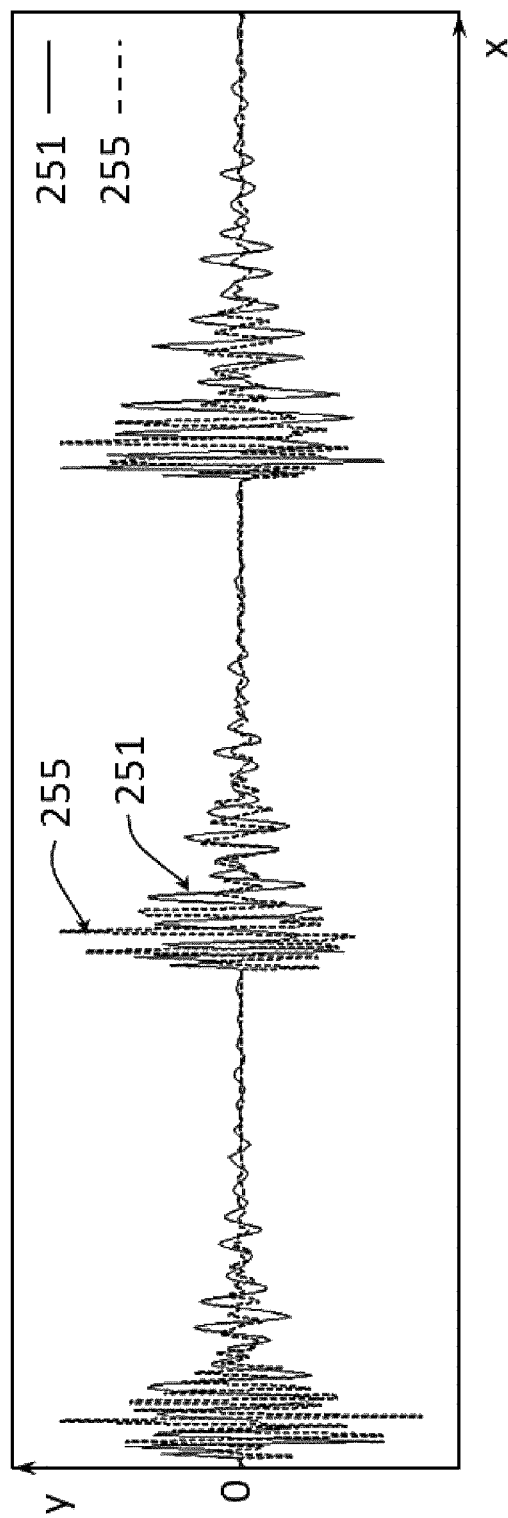
FIG. 9B shows a graphical representation of response functions of two different medical devices comprising multiple ultrasound emitter/sensor elements.

For a medical device, having an identification characteristic based on a combination of individual identification characteristics of multiple ultrasound emitter/sensor elements, the identification characteristics determined at various instances shows great similarity. In FIG. 9A a graphical representation shows an overlap of response functions determined at two different instances for a medical device comprising three ultrasound emitter/sensor elements (FIG. 6A), which then results in very similar identification characteristics too. On the other hand, two different medical devices having similar configurations present dissimilar response functions 251 and 255, graphically illustrated in FIG. 9B.

In an implementation embodiment of the invention, the identification of a medical device can be based on a quadratic norm of the difference between the feature vector of the medical device subject to identification and the feature vectors of known medical devices from the database. The quadratic norm is computed according to $$Q_i = \|\vec{F} - \vec{F_i}\|_2; \quad i=1 \ldots q \tag{Eq. 6}$$

where q is the maximum number of medical devices in the database. When $Q_i$ is smaller than a fixed threshold $\vartheta$, then the medical device is identical to the i-th medical device in the database. For efficiency reasons the computation of further quadratic norms may be omitted when the medical device has been identified.

The threshold value $\vartheta$ can be determined by taking a large set of medical devices comprising ultrasound emitter/sensor elements, preferably more than one hundred (q>100), and by measuring the RF detection signal lines at two relevantly different time instances $t_1$ and $t_2$ by applying identical drive signal to the ultrasound emitter/sensor elements. After obtaining the response functions and the feature vectors of the medical devices, for all pairs of medical devices i and j the quadratic norm can be computed. For q number of medical devices at two different instances one obtains q×q quadratic norm values. The parameter $\vartheta$ is chosen such that two classes are separated on the basis of the quadratic norm values, where the first class comprises identical medical device pairs i, i at the two different time instances, with quadratic norm $$\|\vec{F_i(t_1)} - \vec{F_i(t_2)}\|_2 < \vartheta, \tag{Eq. 7.1}$$

and the second class comprises dissimilar medical device pairs i,j (i≠j) irrespective of the time instance, with quadratic norm $$\|\vec{F_i(t_1 \text{ or } t_1)} - \vec{F_j(t_1 \text{ or } t_2)}\|_2 > \vartheta. \tag{Eq. 7.2}$$

Figure 10A:
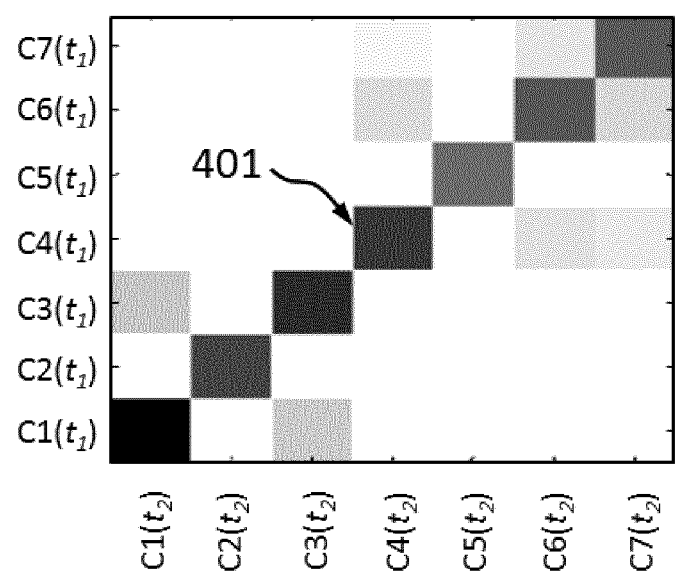
FIGS. 10A and 10B show exemplarily representations of the quadratic norm of feature vector differences used for identification of medical devices.
Figure 10B:
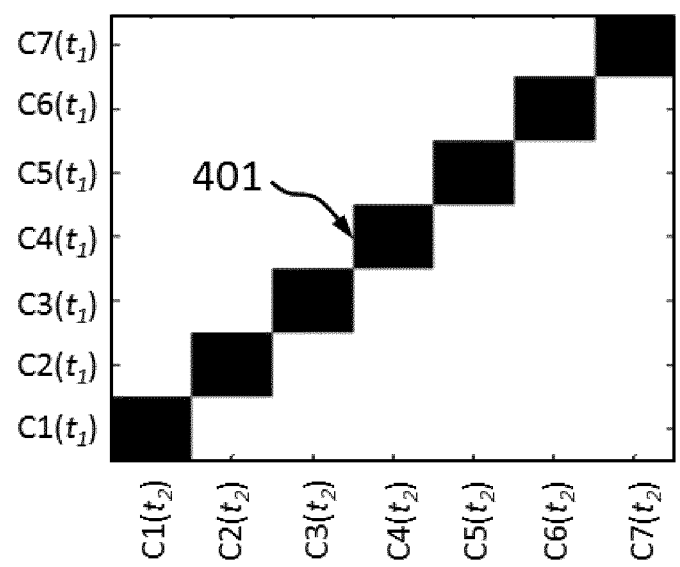

FIGS. 10A and 10B show exemplarily the result of identification of seven different medical devices with configuration shown in FIG. 6A. The medical devices are catheters comprising an axially oriented 321 and two radially oriented 322,323 ultrasound emitter/sensor elements for ultrasound imaging of heart anatomy. At a first instance $t_1$ the catheters are coupled to the apparatus 2 which is arranged to send drive signal to the ultrasound emitter/sensor elements and to receive detection signals from the ultrasound emitter/sensor elements. The processor is arranged to compute a feature vector for each catheter based on Eq. 1-5, which are assigned as identification characteristics $C1(t_1) \ldots C7(t_1)$ of the catheters at time instance $t_1$. These identifications characteristics are stored in the form of a database 211 in the internal memory 21 of the apparatus 2. At a second instance $t_2$ the same seven catheters are coupled to the apparatus 2, which is arranged to send identical drive signal to the ultrasound emitter/sensor elements as in the first instance $t_1$. The received detection signals from the ultrasound emitter/sensor elements are processed and a feature vector for each catheter is computed based on Eq. 1-5, which are then assigned as identification characteristics $C1(t_2) \ldots C7(t_2)$ of the catheters at time instance $t_2$. The processor is operable to compute the quadratic norm of the feature vector differences of each and every possible catheter pairs for the two different time instances according to Eq. 6, such that in any catheter pair one of the identification characteristic is for the first instance $t_1$ and the other one is for the second instance $t_2$. FIG. 10A shows a representation of the quadratic norm of feature vector differences. A demarcation of darker rectangles 401 can be observed on the diagonal of the graphical representation, with the significance that for comparison of identical catheters at two different instances $t_1$ and $t_2$ the value of the quadratic norm is low.

Upon using the threshold value ϑ determined with Eq. 7.1 and Eq. 7.2, a binary separation between similar and dissimilar catheter identification characteristics can be obtained, as shown in FIG. 10B.

Identification of medical devices represents a necessary step when logging the use of medical devices is required for safety reasons. The system 1, shown in FIG. 1, enables tracking of use of a medical device. The processor 22 is operable to identify a medical device from the database 211 or 511 based on the identification characteristic when the medical device 3 is coupled to the apparatus 2. Once the medical device is identified, the processor is operable to update information in the database about the duration of use of the medical device. Upon multiple coupling of the medical device 3 to the apparatus 2, in similar way, the processor may be arranged to update the frequency of use of the medical device in the database.

In a further embodiment of the invention the processor is operable to send a warning signal to the user of the system when a predetermined use of a medical device is exceeded. The warning signal may be a visual signal or a text displayed on a screen 7 of the system. Alternatively, the warning signal may be an audible signal transmitted through a loudspeaker integrated into one of the components of the system 1, or it may be a tactile feedback such as mechanical vibrations on the handgrip at the proximal end 31 of the medical device 3.

In another embodiment of the invention the apparatus 2 is operable to communicate with the external server 5 and to update the database 511 of known identification characteristics of medical devices with a warning message for use of a medical device exceeding the predetermined limit. The main benefit is the possibility for logging the use of medical devices deviating from the recommended limitation, indifferent from how the user of the system reacts upon prompted warning signals.

In an alternative embodiment of the system, the apparatus is arranged to discontinue the use of at least one ultrasound emitter/sensor element when a predetermined use of the medical device is exceeded. Various mechanisms may be used for discontinuing the use of ultrasound emitter/sensor elements. The processor is operable to identify the medical device subjected to use and it is further arranged to check from the database 211 or 511 the data logged on the use of the medical device. When the predetermined use of the medical device is reached or exceeded, the apparatus is arranged to prohibit the transmission of drive signal to the ultrasound emitter/sensor element integrated into the medical device 3. In an alternative embodiment the apparatus is arranged to allow transmission of drive signal to the ultrasound emitter/sensor element, but it obstructs displaying ultrasound information on the screen 7. In yet another embodiment the apparatus is arranged to change the drive signal to a very short and high voltage signal when the predetermined use of the device is exceeded, resulting in depoling of the active part of the ultrasound emitter/sensor element, hence in the inability to generate ultrasound waves upon further receiving any drive signal.

Figure 11:
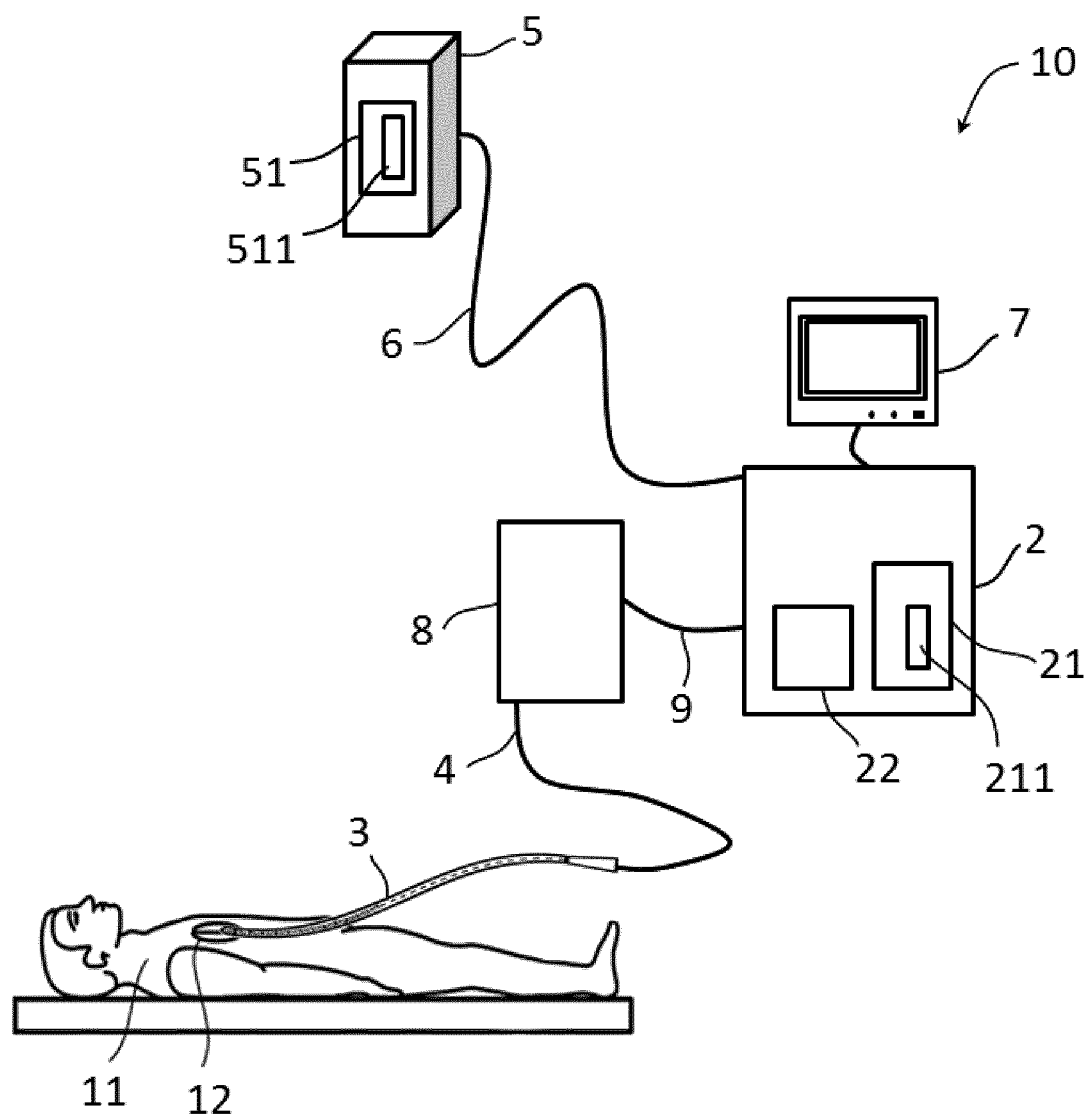
FIG. 11 shows schematically and exemplarily an embodiment of a system for identification of a medical device for energy application to a heart tissue.

FIG. 11 shows an embodiment of a system 10 comprising besides the components of the system 1 an energy source unit 8 connected to the apparatus 2 with transmission path 9. The energy source unit 8, connected to the medical device 3 through connection path 4, can provide radiofrequency current to the electrical conductive casing 329 at the distal end 32 of the medical device. A neutral electrode (not shown) placed on the body of the living being 11 and connected to the energy source unit 8 ensures that the electrical circuit is closed through the body of the living being. The energy source unit is operable to transmit a radiofrequency current to heat locally the heart 12 tissue at the contact of the heart tissue with the casing 329 at the distal end 32 of the medical device 3. The energy source unit 8 in similar embodiments may be arranged to provide energy to the medical device in the form of electromagnetic radiation.

When a medical device 3 coupled to the system 10 is identified from the database 211 or 511 as a medical device that exceeded its predetermined use, the apparatus 2 is arranged to disable transmission of energy from the energy source unit 8 to the medical device, consequently prohibiting energy application for heating the heart tissue. This may be achieved by the processor of the apparatus 2 operable to send a signal to a processor of the energy source unit 8, which upon receiving the signal prohibits transmission of energy from the energy source unit 8 to the medical device 3. A medical device operable to apply energy to heart tissue may potentially be a single use disposable device. Unsafe use of a medical device is discouraged by recognizing the medical device attempted to be used in an inappropriate manner, followed by subsequently prohibiting transmission of energy to the medical device.

Other variations to the disclosed embodiments can be understood and effected by those skilled in the art in practicing the claimed invention, from a study of the drawings, the disclosure, and the appended claims.

Medical devices may be devices comprising ultrasound emitter/sensor elements used either inside or outside of the body of living beings. Functional use of a medical device may be ultrasound imaging, photoacoustical imaging, ultrasound based tracking of devices, interventional use such as energy application to a tissue by high intensity ultrasound waves or by any other energy form, combined with ultrasound monitoring of tissue property change upon energy application. For interventional medical devices comprising ultrasound emitter/sensor elements it is beneficial to use already integrated elements and electronics in the system for identification purposes, rather than integrating additional devices like microchips together with readout and controlling electronics. Ultrasound emitter/sensor elements used for identification of medical devices may not necessarily need to be integrated into the distal end 32 of the medical device 3, as they may be integrated alternatively in any structural part of the medical device, including the handgrip at the proximal end 31.

A single unit or device may fulfill the functions of several items recited in the claims. The mere fact that certain measures are recited in mutually different dependent claims does not indicate that a combination of these measures cannot be used to advantage.

In the claims, the word "comprising" does not exclude other elements or steps, and the indefinite article "a" or "an" does not exclude a plurality.

Any reference signs in the claims should not be construed as limiting the scope.

The invention claimed is:

1. A system for recognizing an identification characteristic of a medical device carrying an ultrasound element, said system comprising:
    an apparatus arranged to be operatively coupled to the medical device, and arranged to send a drive signal to the ultrasound element and to receive a detection signal from the ultrasound element,
    wherein the apparatus comprises a processor operable to:
        process detection signals from the ultrasound element to determine the identification characteristic of the medical device; and recognize the identification characteristic of the medical device from a database of known identification characteristics of medical devices subsequent to a coupling of the medical device to the apparatus, wherein the ultrasound element comprises an active part and a passive part, wherein an acoustic coupling layer of the passive part is fixed on a surface of the active part, and wherein the identification characteristic is representative of the passive part of the ultrasound element.

2. System according to claim 1, wherein the identification characteristic of the medical device is determined based on detection signals from the ultrasound element and at least one additional ultrasound element of the medical device, wherein the ultrasound element and the at least one additional ultrasound element are oriented in different directions.

3. System according to claim 1, wherein the identification characteristic of the medical device is determined based on detection signals from at least one ultrasound element originating from a piezoelectric ultrasound element array or from a capacitive micro-machined ultrasound array.

4. System according to claim 1, wherein the identification characteristic is a feature vector.

5. System according to claim 1, wherein the identification characteristic is determined for the medical device based on detection signals received from an ultrasound element comprising at least an acoustical coupling material.

6. System according to claim 1, wherein the processor is operable to update the database of known identification characteristics of medical devices by adding to the database the identification characteristic of the medical device coupled to the apparatus.

7. System according to claim 1, wherein the apparatus comprises an internal memory unit, wherein the database of known identification characteristics of medical devices is stored in the internal memory unit of the apparatus.

8. System according to claim 1, wherein the apparatus is in communication with an external server, wherein the database of known identification characteristics of medical devices is stored on the external server, and wherein the apparatus is arranged to communicate with the external server for transmitting and/or receiving at least the identification characteristic of the medical device.

9. System according to claim 8, wherein a transmission path between the medical device and the apparatus and/or a transmission path between the apparatus and the external server is arranged through wireless connection.

10. System according to claim 1, wherein the processor is operable to recognize the identification characteristic of the medical device from the database based on a quadratic norm of feature vector differences.

11. System according to claim 1, wherein the processor is operable to update information in the database about a duration and a frequency of use of the medical device.

12. System according to claim 11, wherein the processor is operable to send a warning signal to the user of the system when a predetermined limit of use of the medical device is exceeded.

13. System according to claim 11, wherein the apparatus is operable to update the database of known identification characteristics of medical devices on an external server with a warning message for use of the medical device exceeding the predetermined limit.

14. System according to claim 1, wherein the apparatus is arranged to discontinue the use of the ultrasound element when a predetermined limit of use of the medical device is exceeded.

15. System according to claim 1, wherein the system further comprises an energy source unit for energy application to a tissue, and wherein the apparatus is arranged to disable transmission of energy from the energy source unit to the medical device when a predetermined limit of use of the medical device is exceeded.

\* \* \* \* \*